(12) United States Patent
Lee et al.

(10) Patent No.: US 11,813,067 B2
(45) Date of Patent: Nov. 14, 2023

(54) SYSTEM AND METHOD FOR ALZHEIMER'S DISEASE PREDICTION USING NEURAL NETWORK, COMPUTER-READABLE RECORDING MEDIUM WITH STORED PROGRAM, AND COMPUTER PROGRAM PRODUCT

(71) Applicant: National Cheng Kung University, Tainan (TW)

(72) Inventors: Gwo-Giun Lee, Tainan (TW); Yi-Ru Xie, Tainan (TW); Yu-Min Kuo, Tainan (TW)

(73) Assignee: National Cheng Kung University, Tainan (TW)

( * ) Notice: Subject to any disclaimer, the term of this patent is extended or adjusted under 35 U.S.C. 154(b) by 49 days.

(21) Appl. No.: 17/335,700

(22) Filed: Jun. 1, 2021

(65) Prior Publication Data
US 2022/0378361 A1    Dec. 1, 2022

(51) Int. Cl.
*A61B 5/00* (2006.01)
*A61B 5/055* (2006.01)

(52) U.S. Cl.
CPC .......... *A61B 5/4088* (2013.01); *A61B 5/0042* (2013.01); *A61B 5/055* (2013.01); *A61B 5/7267* (2013.01); *A61B 5/7275* (2013.01)

(58) Field of Classification Search
None
See application file for complete search history.

(56) References Cited

U.S. PATENT DOCUMENTS

2022/0051801 A1* 2/2022 Feng ................. G06N 3/02
2022/0281733 A1* 9/2022 Bauchot ............ B67D 1/0022

FOREIGN PATENT DOCUMENTS

CN        110969626 A  *  4/2020  ........... G06N 3/0454

OTHER PUBLICATIONS

Guo et al., "Identifying subtypes of mild cognitive impairment from healthy aging based on multiple cortical features combined with volumetric measurements of the hippocampal subfields," (Jul. 2020), Quant Imaging Med Surg 2020;10(7):1477-1489. (Year: 2020).*

(Continued)

*Primary Examiner* — Joel Lamprecht
*Assistant Examiner* — Ashish S Jasani
(74) *Attorney, Agent, or Firm* — RABIN & BERDO, P.C.

(57) ABSTRACT

A system and a method for Alzheimer's disease prediction using a neural network, a computer-readable recording medium with a stored program, and a computer program product are provided. The processor obtains a first brain MRI data, a second brain MRI data, a first neuropsychological assessment score, and a second neuropsychological assessment score. The processor obtains a plurality of image feature data according to the first brain MRI data and the second brain MRI data. Each image feature data is selected from a group consisting of a plurality of hippocampal subfield geometric change data. The processor obtains a neuropsychological change data according to the first neuropsychological assessment score and the second neuropsychological assessment score. The processor obtains an Alzheimer's disease prediction result according to the neural network module, the image feature data, and the neuropsychological change data.

22 Claims, 6 Drawing Sheets

(56) References Cited

OTHER PUBLICATIONS

Khan et al., "Automated Hippocampal Subfield Measures as Predictors of Conversion from Mild Cognitive Impairment to Alzheimer's Disease in Two Independent Cohorts," (Nov. 5, 2015), Brain Topogr (2015) 28:746-759. (Year: 2015).*

Kwak et al., "Differential Role for Hippocampal Subfields in Alzheimer's Disease Progression Revealed with Deep Learning," (Jul. 29, 2021), Cerebral Cortex, Mar. 2022;32: 467-478. (Year: 2021).*

Mukhtar et al., "Convolutional Neural Network Based Prediction of Conversion from Mild Cognitive Impairment to Alzheimer's Disease: A Technique using Hippocampus Extracted from MRI," (May 2020), Advances in Electrical and Computer Engineering vol. 20, No. 2, 2020 (Year: 2020).*

Platero et al., "Discriminating Alzheimer's disease progression using a new hippocampal marker from T1-weighted MRI: The local surface roughness," (Apr. 1, 2019), Hum Brain Mapp. 2019;40:1666-1676. (Year: 2019).*

Varma et al., "Hippocampal Sub-Regional Shape and Physical Activity in Older Adults," (Aug. 5, 2019), Hippocampus. Aug. 2016 ; 26(8): 1051-1060. (Year: 2019).*

Xu et al., "Longitudinal volume changes of hippocampal subfields and cognitive decline in Parkinson's disease," (Jan. 2020), Quant Imaging Med Surg 2020;10(1):220-232. (Year: 2020).*

Moore et al., "Random forest prediction of Alzheimer's disease using pairwise selection from time series data," ( Feb. 14, 2019), PLoS One. 2019; 14(2): e0211558. (Year: 2019).*

* cited by examiner

Obtain a first brain magnetic resonance imaging (MRI) data, a second brain MRI data, a first neuropsychological assessment score, and a second neuropsychological assessment score, where the first neuropsychological assessment score has a first time marker, the second neuropsychological assessment score has a second time marker, the first brain MRI data corresponds to the first time marker, and the second brain MRI data corresponds to the second time marker ~S501

Obtain a plurality of image feature data according to the first brain MRI data and the second brain MRI data, where each image feature data is selected from a group consisting of a plurality of hippocampal subfield curvature change data of a plurality of hippocampal subfields, a plurality of hippocampal subfield volume change data of the plurality of hippocampal subfields, and a plurality of hippocampal subfield surface area change data of the plurality of hippocampal subfields ~S502

Obtain a neuropsychological change data according to the first neuropsychological assessment score and the second neuropsychological assessment score ~S503

Obtain an Alzheimer's disease prediction result according to a neural network module, the plurality of image feature data, and the neuropsychological change data ~S504

FIG.5

```
┌─────────────────────────────────────────────────┐
│  Obtain a plurality of groups of historical data, │
│ each group of historical data including third brain MRI │
│ data, fourth brain MRI data, a third neuropsychological │
│        assessment score, a fourth neuropsychological     │
│ assessment score, and an Alzheimer's marker, where the   │──S601
│   third neuropsychological assessment score has a third  │
│    time marker, the fourth neuropsychological assessment │
│   score has a fourth time marker, the third brain MRI data│
│     corresponds to the third time marker, and the fourth │
│      brain MRI data corresponds to the fourth time marker│
└─────────────────────────────────────────────────┘
                          ↓
┌─────────────────────────────────────────────────┐
│  Based on each biomarker of a plurality of biomarkers,   │
│       extract a plurality of first corresponding data    │
│ corresponding to the third time marker from the third brain│──S602
│  MRI data in the plurality of historical data, and extract a│
│    plurality of second corresponding data corresponding to│
│     the fourth time marker from the fourth brain MRI data │
└─────────────────────────────────────────────────┘
                          ↓
┌─────────────────────────────────────────────────┐
│    Select a plurality of training biomarkers from the    │──S603
│      biomarkers according to a selection algorithm       │
└─────────────────────────────────────────────────┘
                          ↓
┌─────────────────────────────────────────────────┐
│  Obtain a plurality of biomarker change data based on the│
│   plurality of first corresponding data and the plurality of│
│   second corresponding data of each training biomarker;  │
│  and obtain a plurality of historical neuropsychological │──S604
│       change data based on the third neuropsychological  │
│        assessment score and the fourth neuropsychological│
│      assessment score in each group of historical data   │
└─────────────────────────────────────────────────┘
                          ↓
┌─────────────────────────────────────────────────┐
│    Train the neural network module by using the          │
│   plurality of biomarker change data, the plurality of   │
│     historical neuropsychological change data, and the   │──S605
│     Alzheimer's marker of each group of historical data  │
└─────────────────────────────────────────────────┘
```

FIG.6

SYSTEM AND METHOD FOR ALZHEIMER'S DISEASE PREDICTION USING NEURAL NETWORK, COMPUTER-READABLE RECORDING MEDIUM WITH STORED PROGRAM, AND COMPUTER PROGRAM PRODUCT

BACKGROUND

Technical Field

The present invention relates to prediction of the Alzheimer's disease by using a neural network, and in particular, to the prediction of transformation from mild cognitive impairment to Alzheimer's disease for a patient by using the neural network technology in combination with neuroimaging biomarkers and neuropsychological biomarkers.

Related Art

Alzheimer's disease (AD) is characterized by memory loss, cognitive impairment, and behavioral changes. As of 2019, 50 million people have dementia, and there are nearly 9 million new cases. Accompanied with population aging in next few years, these numbers will increase rapidly, and this disease is the seventh leading cause of death in the United States. AD pathology is characterized by extracellular amyloid beta (Aβ) neuritic plaques and intracellular neurofibrillary tangles. The Aβ plaques are toxic and gradually accumulate in the brain throughout the course of the disease, destroying connections between neurons, and even causing neuronal death. Excessive Aβ accumulation eventually involves much of the neocortex, hippocampus, and many subcortical structures.

Early-stage AD is more difficult to diagnose. Clinical symptoms appear after significant deposition of Aβ has already occurred. The ability to detect early-stage AD in a specific and sensitive manner prior to the occurrence of significant impairment, and the advent of new therapeutic agents that work by arresting Aβ accumulation or depletion of Aβ levels in the brain, are important to early treatment and inhibition of disease progression.

Magnetic resonance imaging (MRI) uses a radiologic technique to record the emission of energy from brain neurons or blood flow which is placed within a magnetic field. MRI makes better images of organs and soft tissue such as fat and body fluids in comparison to X-ray, computed tomography, and ultrasound imaging. MRI is a non-invasive imaging technology and can acquire images in multiple planes without repositioning a patient.

Neuropsychological assessment is an in-depth assessment, which refers to the measurement of cognitive functions in the brain. The aim of neuropsychological assessment is to determine whether cognitive impairment is present in individuals and identify strengths and weakness across multiple areas.

Therefore, it is necessary to develop a method and system that can integrate MRI image information and neuropsychological assessment to predict AD and assist in treatment decision-making for subjects at risk of AD.

SUMMARY

In view of this, the present invention provides a system for Alzheimer's disease prediction using a neural network, a method for Alzheimer's disease prediction using a neural network, a computer-readable recording medium with a stored program, and a computer program product, to alleviate existing technical problems.

According to some embodiments, a system for Alzheimer's disease prediction using a neural network is provided. The system for Alzheimer's disease prediction using a neural network includes a processor and a neural network module. The processor is configured to obtain a first brain MRI data, a second brain MRI data, a first neuropsychological assessment score, and a second neuropsychological assessment score, where the first neuropsychological assessment score has a first time marker, the second neuropsychological assessment score has a second time marker, the first brain MRI data corresponds to the first time marker, and the second brain MRI data corresponds to the second time marker. The neural network module has a plurality of trained parameters. The processor is configured to execute the following steps: obtaining a plurality of image feature data according to the first brain MRI data and the second brain MRI data, where each image feature data is selected from a group consisting of a plurality of hippocampal subfield curvature change data of a plurality of hippocampal subfields, a plurality of hippocampal subfield volume change data of the plurality of hippocampal subfields, and a plurality of hippocampal subfield surface area change data of the plurality of hippocampal subfields; obtaining a neuropsychological change data according to the first neuropsychological assessment score and the second neuropsychological assessment score; and obtaining an Alzheimer's disease prediction result according to the neural network module, the plurality of image feature data, and the neuropsychological change data.

According to some embodiments, a method for Alzheimer's disease prediction using a neural network is provided. The method for Alzheimer's disease prediction using a neural network is performed by a processor and includes the following steps: obtaining a first brain MRI data, a second brain MRI data, a first neuropsychological assessment score, and a second neuropsychological assessment score, where the first neuropsychological assessment score has a first time marker, the second neuropsychological assessment score has a second time marker, the first brain MRI data corresponds to the first time marker, and the second brain MRI data corresponds to the second time marker; obtaining a plurality of image feature data according to the first brain MRI data and the second brain MRI data, where each image feature data is selected from a group consisting of a plurality of hippocampal subfield curvature change data of a plurality of hippocampal subfields, a plurality of hippocampal subfield volume change data of the plurality of hippocampal subfields, and a plurality of hippocampal subfield surface area change data of the plurality of hippocampal subfields; obtaining a neuropsychological change data according to the first neuropsychological assessment score and the second neuropsychological assessment score; and obtaining an Alzheimer's disease prediction result according to a neural network module, the plurality of image feature data, and the neuropsychological change data.

According to some embodiments, a computer-readable recording medium stores a stored program, when a computer loads and executes the stored program, the foregoing method for Alzheimer's disease prediction using a neural network can be performed.

According to some embodiments, a program product stores a computer program, and when a computer loads and executes the computer program, the foregoing method for Alzheimer's disease prediction using a neural network can be performed.

According to some embodiments, the system for Alzheimer's disease prediction using a neural network, the method for Alzheimer's disease prediction using a neural network, the computer-readable recording medium with a stored program, and the computer program product use the neural network to integrate MRI image information and neuropsychological assessment for Alzheimer's disease prediction.

BRIEF DESCRIPTION OF THE DRAWINGS

FIG. 5 is a flowchart of steps according to an embodiment of the present invention; and FIG. 6 is a flowchart of steps of training a neural network module according to an embodiment of the present invention.

DETAILED DESCRIPTION

The foregoing and other technical contents, features, and effects of the present invention can be clearly presented below in detailed description with reference to embodiments of the accompanying drawings. The term "connect" provided in the following embodiments may refer to any direct or indirect connection means.

Figure 1:
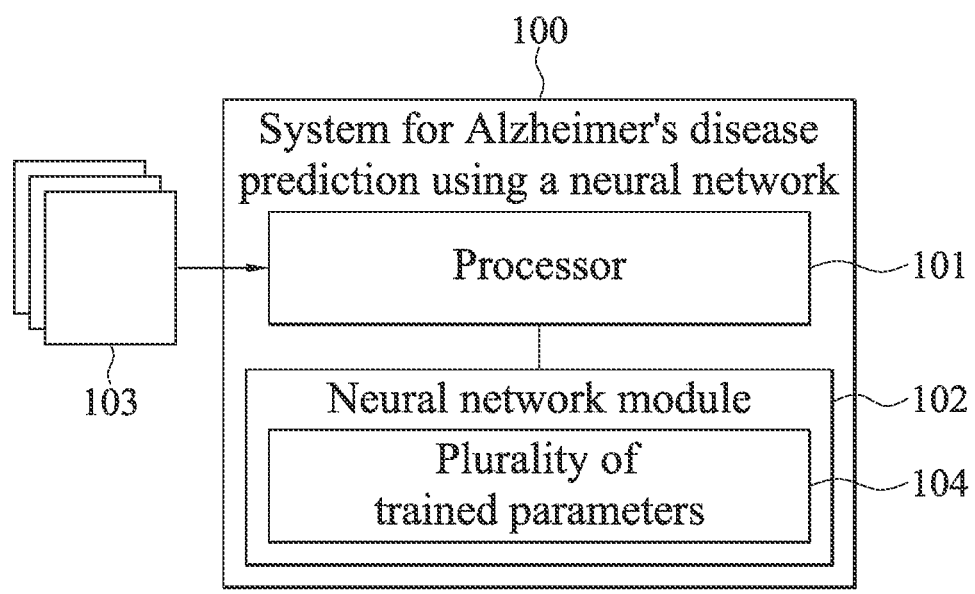
FIG. 1 is a block diagram of a system for Alzheimer's disease prediction using a neural network according to an embodiment of the present invention.

FIG. 1 is a block diagram of a system for Alzheimer's disease prediction using a neural network according to an embodiment of the present invention. Referring to FIG. 1, a system 100 for Alzheimer's disease prediction using a neural network includes a processor 101 and a neural network module 102. The neural network module 102 further includes a plurality of trained parameters 104. The processor 101 may receive data 103 from the outside.

Neuropsychological assessment is an in-depth assessment, which refers to the measurement of cognitive functions in the brain. The aim of neuropsychological assessment is to determine whether cognitive impairment is present in individuals and identify strengths and weakness across multiple areas. Neuropsychological assessment that is frequently used at present includes Mini-Mental State Examination (MMSE) and Clinical Dementia Rating (CDR).

MMSE is an assessment tool designed for cognitive functions. There are 11 questions in total for cognitive functions, including time and place orientation ability, attention and arithmetic ability, immediate memory and short-term memory, language (including reading, writing, naming, comprehension, and manipulation) ability, and visual space ability. MMSE only takes 5 to 10 minutes. The highest score is 30. The higher the score, the better the ability.

CDR is a semi-structured questionnaire for accessing disability of patients with dementia. A degree of cognitive degradation of a patient is determined by interacting with the patient, and severity of a patient with dementia is evaluated according to information provided by the family of the patient. The advantage is oriented assessment for daily life and cognitive functions.

Figure 2:
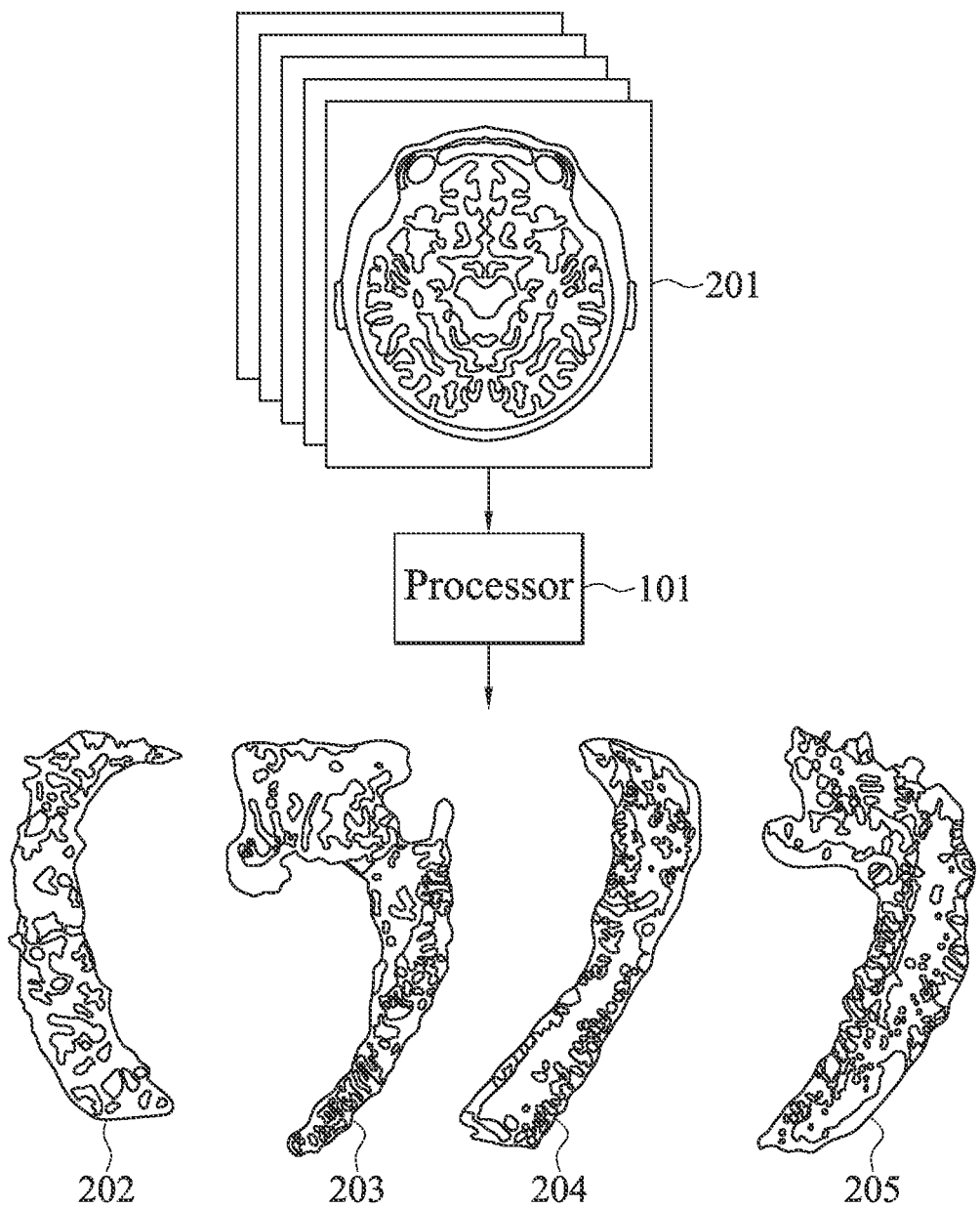
FIG. 2 is a schematic operation diagram of a processor according to an embodiment of the present invention.

FIG. 2 is a schematic operation diagram of a processor 101 according to an embodiment of the present invention. Referring to FIG. 2, the processor 101 may obtain brain MRI data 201 from the outside. The processor 101 performs image processing on the obtained MRI data 201 and can obtain a 3D model of each subfield in the brain. For example, as shown in FIG. 2, the processor 101 obtains 3D models of hippocampal subfields, including Presubiculum 204, Subiculum 202, CA1 (Cornu Ammonis 1) 203, and CA3 (Cornu Ammonis 3) 205, in the brain through calculation. The processor 101 may call a function of FreeSurfer to perform the image processing. Functions of FreeSurfer are only a conventional technology in the field of image processing, and further description may be obtained with reference to the instruction manual of FreeSurfer.

Figure 3A:
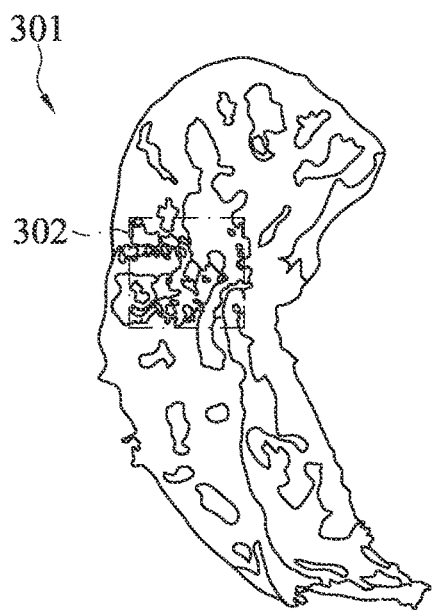
FIG. 3A is a schematic diagram of a 3D model according to an embodiment of the present invention.
Figure 3B:
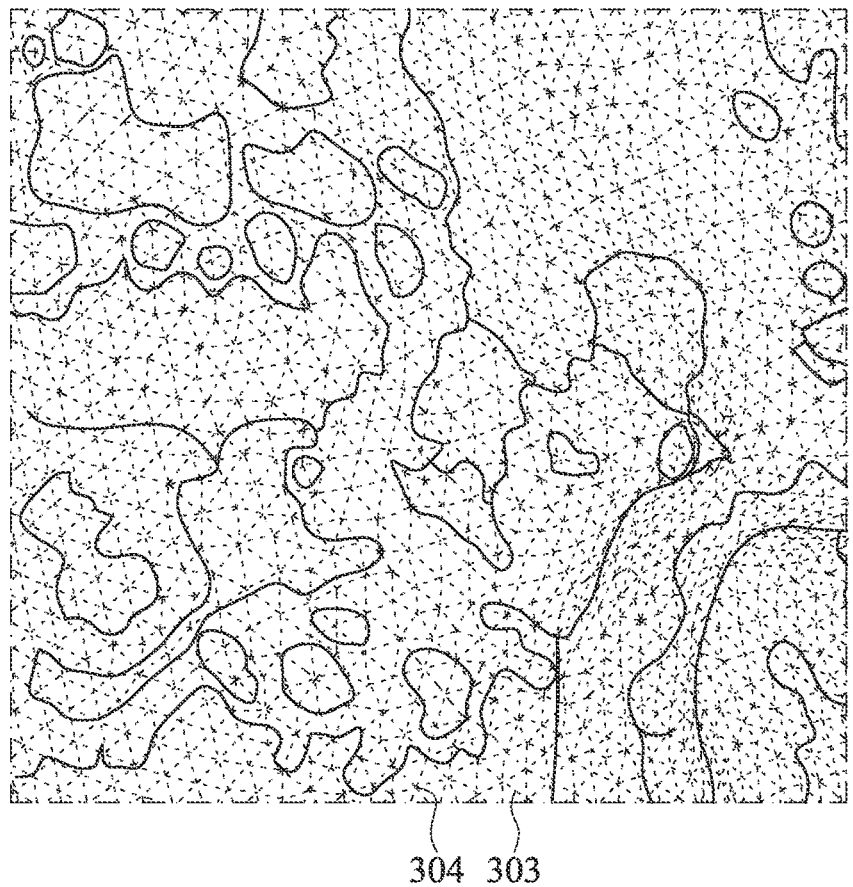
FIG. 3B is an enlarged view of a 3D model surface.

FIG. 3A is a schematic diagram of a 3D model according to an embodiment of the present invention. Referring to FIG. 3A, a 3D subfield model 301 is a 3D brain subfield model obtained by the processor 101 according to an embodiment of the present invention. A 3D model surface 302 is a partial surface of the 3D subfield model 301. FIG. 3B is an enlarged view of the 3D model surface 302. As shown in FIG. 3B, the 3D model surface of a brain subfield obtained by the processor 101 is actually composed of many meshes 303, and each mesh 303 has a plurality of vertexes 304.

Mathematically, for each point on a curved smooth surface, three types of curvatures can be defined, including: a maximum principal curvature, a minimum principal curvature, and a ratio of principal curvatures. Definitions of the three types of curvatures can refer to any differential geometry book. For the 3D model surface of a brain subfield obtained by the processor 101, the processor 101 may calculate a maximum principal curvature, a minimum principal curvature, and a ratio of principal curvatures of each vertex 304.

Figure 4:
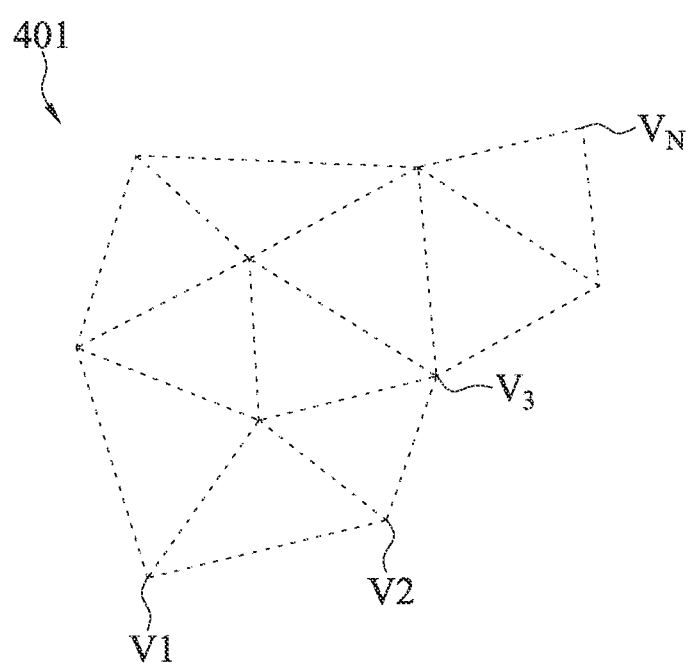
FIG. 4 is a schematic diagram of meshes of a 3D model surface of a brain subfield according to an embodiment of the present invention.

FIG. 4 is a schematic diagram of meshes of a 3D model surface of a brain subfield according to an embodiment of the present invention. Referring to FIG. 4, the 3D model surface of a brain subfield obtained by the processor 101 may be extended to a mesh map 401 as shown in FIG. 4. The mesh map 401 has grid points $V_1, V_2, \ldots,$ and $V_N$. In the present invention, a maximum principal curvature of a brain subfield is defined as an average value of maximum principal curvatures of the grid points $V_1, V_2, \ldots,$ and $V_N$. A minimum principal curvature of a brain subfield is defined as an average value of minimum principal curvatures of the grid points $V_1, V_2, \ldots,$ and $V_N$. A ratio of principal curvatures of a brain subfield is defined as an average value of ratios of principal curvatures of the grid points $V_1, V_2, \ldots,$ and $V_N$.

For example, the maximum principal curvatures of the grid points $V_1, V_2, \ldots,$ and $V_N$ are respectively $C_1, C_2, \ldots,$ and $C_N$, and the maximum principal curvature C of the brain subfield where the grid points $V_1, V_2, \ldots,$ and $V_N$ are located is:

$$C = \frac{C_1 + C_2 + \ldots C_N}{N}. \tag{1}$$

The maximum principal curvature, the minimum principal curvature, and the ratio of principal curvatures of the foregoing brain subfield may be obtained through calculation by using a function of FreeSurfer called by the processor 101. The function of FreeSurfer also provides a function of calculating a volume and a surface area of a brain subfield.

FIG. 5 is a flowchart of steps according to an embodiment of the present invention. Refer to FIG. 1 to FIG. 5. In an embodiment of the present invention, in step S501, the processor 101 obtains from the outside first brain MRI data and a first neuropsychological assessment score of a to-be-predicted patient when the to-be-predicted patient is diagnosed with mild cognitive impairment (MCI). A first visit time when the to-be-predicted patient is diagnosed with MCI is a first time marker.

The processor 101 then obtains from the outside second brain MRI data and a second neuropsychological assessment score of the to-be-predicted patient when the to-be-predicted patient visits a doctor again after a specific period of time. A second visit time of the to-be-predicted patient is a second time marker.

In step S502, the processor 101 constructs a 3D brain model of the to-be-predicted patient in the first visit and the second visit according to the first brain MRI data and the second brain MRI data. The processor 101 selects image features of several subfields in the hippocampus of the brain according to an input required by the neural network module 102. The image features of several subfields in the hippocampus may be maximum principal curvatures, minimum principal curvatures, ratios of principal curvatures, surface areas, and volumes of the subfields in the hippocampus. The several subfields in the hippocampus of the brain may be subfields such as Parasubiculum, Presubiculum, Subiculum, CA1, CA3, CA4 (Cornu Ammonis 4), GC-ML-DG (Granule Cell Molecular Layer of Dentate Gyms), HATA (Hippocampal Amygdala Transition Area), Fimbria, Molecular layer, Hippocampal fissure, and Hippocampal tail. For example, the selected image features are the volume of CA1, the maximum principal curvature of CA1, the surface area of Subiculum, and the volume of Subiculum. The processor 101 then separately calculates image feature data of the to-be-predicted patient in the first visit and the second visit according to the image features and the 3D brain model of the to-be-predicted patient in the first visit and the second visit. For example, the image feature data is volume data of CA1, maximum principal curvature data of CA1, surface area data of Subiculum, and volume data of Subiculum in the first visit, and volume data of CA1, maximum principal curvature data of CA1, surface area data of Subiculum, and volume data of Subiculum in the second visit. The processor 101 then calculates change data of the selected image features according to the image feature data in the first visit and the second visit. For example, the change data is volume change data of CA1, maximum principal curvature change data of CA1, surface area change data of Subiculum, and volume change data of Subiculum obtained by calculating the volume data of CA1, the maximum principal curvature data of CA1, the surface area data of Subiculum, and the volume data of Subiculum in the first visit and the second visit.

In step S503, the processor 101 obtains neuropsychological change data according to the first neuropsychological assessment score and the second neuropsychological assessment score.

In step S504, the processor 101 inputs the plurality of image feature data and the neuropsychological change data to the neural network module 102 to obtain an Alzheimer's disease prediction result.

In some embodiments, the first brain MRI data and the second brain MRI data are respectively MRI images of the to-be-predicted patient in the first visit and the second visit.

A structure of the neural network module 102 may have a plurality of sublayers with different neural network structures. In some embodiments, the neural network module 102 includes a fully connected sublayer with a plurality of hidden layers or a convolutional neural network layer.

In some embodiments, the first neuropsychological assessment score and the second neuropsychological assessment score are scores of MMSE or CDR.

There are many definitions and calculation methods for the change data of the selected image features selected by the processor 101. In an embodiment of the present invention, the change data $C_f$ of the image features is calculated by the following formula (hereafter called as a change data computing procedure):

$$C_f = \frac{f_{second\ visit} - f_{first\ visit}}{f_{first\ visit}}, \quad (2)$$

where $f_{second\ visit}$ represents data of the image features in the second visit, and $f_{first\ visit}$ represents data of the image features in the first visit. For example, if the image feature is the maximum principal curvature of CA1, the maximum principal curvature change data of CA1 is (maximum principal curvature data of CA1 in the second visit-maximum principal curvature data of CA1 in the first visit)/maximum principal curvature data of CA1 in the first visit.

Similarly, there are many definitions and calculation methods for the neuropsychological change data obtained by the processor 101 according to the first neuropsychological assessment score and the second neuropsychological assessment score. In an embodiment of the present invention, the neuropsychological change data $P_g$ is calculated by the following formula (hereafter called as a neuropsychological change data computing procedure):

$$P_g = \frac{g_{second\ visit} - g_{first\ visit}}{g_{first\ visit}}, \quad (3)$$

where $g_{second\ visit}$ represents the second neuropsychological assessment score, and $g_{first\ visit}$ represents the first neuropsychological assessment score.

FIG. 6 is a flowchart of steps of training a neural network module according to an embodiment of the present invention. Referring to FIG. 1 and FIG. 6, a system 100 for Alzheimer's disease prediction using a neural network includes the neural network module 102. The neural network module 102 includes a plurality of trained parameters 104. Before the processor 101 obtains an Alzheimer's disease prediction result by using the neural network module 102, the processor 101 needs to execute a training program to obtain the plurality of trained parameters 104.

The training procedure includes steps S601 to S605. In step S601, the processor 101 obtains a plurality of groups of historical data. Each group of historical data includes third brain MRI data and a third neuropsychological assessment score of a subject when the subject is diagnosed with MCI, fourth brain MRI data and a fourth neuropsychological assessment score of the subject when the subject visits a doctor again after a specific period of time, and an Alzheimer's marker for determining Alzheimer's disease in a second visit. A first visit time when the subject is diagnosed with MCI is a third time marker, and a second visit time of the subject is a fourth time marker.

In step S602, for each group of historical data, the processor 101 constructs a 3D brain model of the subject in the first visit and the second visit according to the third brain MRI data and the fourth brain MRI data. The processor 101 uses volumes, surface areas, maximum principal curvatures, minimum principal curvatures, and ratios of principal curvatures of hippocampal subfields, including Parasubiculum, Presubiculum, Subiculum, CA1, CA4, Ca4, GC-ML-DG, HATA, Fimbria, Molecular layer, Hippocampal fissure, and Hippocampal tail, as biomarkers.

For each biomarker (for example, a volume of Parasubiculum), the processor 101 then extracts a plurality of first corresponding data in the first visit (for example, volumes of Parasubiculum of all subjects in the first visit) and a plurality of second corresponding data in the second visit (for example, volumes of Parasubiculum of all subjects in the second visit) from 3D brain models of all subjects in the first visit and the second visit from the historical data.

In step S603, the processor 101 selects a plurality of training biomarkers from the biomarkers according to a selection algorithm. For example, the processor 101 selects the volume of CA1, the maximum principal curvature of CA1, the surface area of Subiculum, and the volume of Subiculum.

In step S604, the processor 101 then obtains a plurality of biomarker change data (for example, volume change data of CA1, maximum principal curvature change data of CA1, surface area change data of Subiculum, and volume change data of Subiculum of each subject) based on the plurality of first corresponding data and the plurality of second corresponding data of each training biomarker. The processor 101 then obtains historical neuropsychological change data of each subject based on the third neuropsychological assessment score and the fourth neuropsychological assessment score of the each subject in the plurality of historical data.

In step S605, the processor 101 then trains the neural network module 102 by using the plurality of biomarker change data, the plurality of historical neuropsychological change data, and the Alzheimer's marker of each subject in each group of historical data to obtain the plurality of trained parameters 104.

There are many definitions and calculation methods for the plurality of biomarker change data (for example, volume change data of CA1, maximum principal curvature change data of CA1, surface area change data of Subiculum, and volume change data of Subiculum of each subject) obtained by the processor 101. In an embodiment of the present invention, the biomarker change data $B_f$ is calculated by the following formula (hereafter called as a biomarker change data computing procedure):

$$B_f = \frac{f_{second\,visit} - f_{first\,visit}}{f_{first\,visit}}, \quad (4)$$

where $f_{second\,visit}$ represents data of the biomarkers in the second visit, and $f_{first\,visit}$ represents data of the biomarkers in the first visit. For example, the biomarker is the maximum principal curvature of CA1, and then the maximum principal curvature change data of CA1 is (maximum principal curvature data of CA1 in the second visit-maximum principal curvature data of CA1 in the first visit)/maximum principal curvature data of CA1 in the first visit.

Similarly, there are many definitions and calculation methods for the historical neuropsychological change data of each subject obtained by the processor 101 based on the third neuropsychological assessment score and the fourth neuropsychological assessment score of the each subject in the plurality of historical data. In an embodiment of the present invention, the historical neuropsychological change data $H_g$ is calculated by the following formula (hereafter called as a historical neuropsychological change data computing procedure):

$$H_g = \frac{g_{second\,visit} - g_{first\,visit}}{g_{first\,visit}}, \quad (5)$$

where $g_{second\,visit}$ represents the fourth neuropsychological assessment score of a subject, and $g_{first\,visit}$ represents the third neuropsychological assessment score of a subject.

In some embodiments, the selection algorithm includes the following steps: First, for each biomarker (for example, a volume of Parasubiculum), the processor 101 performs a statistical t-test on the plurality of first corresponding data and the plurality of second corresponding data to obtain a p-value. Second, after the processor 101 performs the t-test on first corresponding data and second corresponding data of all biomarkers, the processor 101 selects, according to a critical p-value, a biomarker with a p-value less than the critical p-value from all the biomarkers to obtain the plurality of training biomarkers.

The processor 101 may call a built-in function of Python to perform the statistical t-test on the plurality of first corresponding data and the plurality of second corresponding data. Functions of the built-in function of Python are only a conventional technology in the field of data processing, and further description may be obtained with reference to the instruction manual of Python.

In some embodiments, the critical p-value is 0.01. In some embodiments, the critical p-value is 0.05. In some embodiments, the critical p-value is 0.1.

In some embodiments, the selection algorithm includes the following steps: First, the processor 101 obtains a plurality of first biomarker change data for each subject of each biomarker (for example, volume change data for CA1 of each subject) based on the plurality of first corresponding data and the plurality of second corresponding data.

Second, the processor 101 creates a plurality of random forests for all biomarkers based on the plurality of first biomarker change data of each subject of each biomarker and the Alzheimer marker of each subject, wherein the number of the plurality of random forests is a first number M and each of the plurality of random forests has a plurality of decision tree. The number of the plurality of decision tree is N. Third, the processor 101 obtains a ranking of all biomarkers based on the total Gini importance of the random forests. The total Gini importance can be obtained from the following equation:

$$f_i = \sum_j ni_j, \quad (6)$$

$$ni_j = W_j G_j - W_{left(j)} G - W_{right(j)} G_{right(j)},$$

where $f_i$ means the total Gini importance of feature i, $ni_j$ means Gini importance in certain branch node j of feature i, $W_j$ is the weight in node j, and the left and right is the side of the child node, and G is the Gini impurity.

Fourth, the processor 101 selects, according to the ranking, a predetermined number of selected biomarkers from all the biomarkers to obtain the plurality of training biomarkers.

Processor 101 may call a built-in function in Python's scikit-learn module to create multiple random forests for all biomarkers using the biomarker change data for of each biomarker each subject and the Alzheimer marker for each subject as input, and obtain the total Gini importance.

The function of the functions in Python's scikit-learn module and how to use Python's built-in functions to build random forests are only a conventional technology in the field of data processing and machine learning, as further explained in the Python scikit-learn module's instruction manual.

In some embodiments, the processor 101 obtains biomarker change data for each biomarker for each subject based on the preceding equation (4), the plurality of first corresponding data and the plurality of second corresponding data.

In some embodiments, the processor 101 first excludes three subfields with smallest volumes, and then selects a plurality of training biomarkers from the biomarkers according to the selection algorithm.

In this specification, the term "computer-readable medium" refers to a non-volatile and non-transitory medium, such as a read only memory (ROM), a flash memory, a floppy disk, a hard disk, a compact disk (CD), a digital versatile disc (DVD), a USB flash drive, a database accessible on the Internet, or any other storage medium with the same function known to a person with ordinary knowledge in the technical field of the present invention. These and other various forms of computer-readable media may involve carrying one or more sequences of one or more instructions to the processor 101 for execution. These instructions embodied in the media are usually referred to as "computer program code" or "computer program product". The "computer program code" or "computer program product" may be a file that can be transmitted over the network, or may be stored in a non-transitory computer-readable storage medium. When these instructions are executed, the processor 101 can perform the steps or functions described in the present invention.

What is claimed is:

1. A system for Alzheimer's disease prediction using a neural network, comprising:
    a processor, configured to obtain a first brain magnetic resonance imaging (MRI) data, a second brain MRI data, a first neuropsychological assessment score, and a second neuropsychological assessment score, wherein the first neuropsychological assessment score has a first time marker, the second neuropsychological assessment score has a second time marker, the first brain MRI data corresponds to the first time marker, and the second brain MRI data corresponds to the second time marker; and
    a neural network module, having a plurality of trained parameters;
    the processor being configured to:
        obtain a plurality of image feature data according to the first brain MRI data and the second brain MRI data, wherein each image feature data is selected from a group consisting of a plurality of hippocampal subfield curvature change data of a plurality of hippocampal subfields, a plurality of hippocampal subfield volume change data of the plurality of hippocampal subfields, and a plurality of hippocampal subfield surface area change data of the plurality of hippocampal subfields;
        obtain a neuropsychological change data according to the first neuropsychological assessment score and the second neuropsychological assessment score; and
        obtain an Alzheimer's disease prediction result according to the neural network module, the plurality of image feature data, and the neuropsychological change data,
    wherein the neural network module comprises the plurality of trained parameters, and the processor executes a training procedure on the neural network module to obtain the plurality of trained parameters, the training procedure comprising:
        obtaining a plurality of groups of historical data, each group of historical data comprising a third brain MRI data, a fourth brain MRI data, a third neuropsychological assessment score, a fourth neuropsychological assessment score, and an Alzheimer's marker, wherein the third neuropsychological assessment score has a third time marker, the fourth neuropsychological assessment score has a fourth time marker, the third brain MRI data corresponds to the third time marker, and the fourth brain MRI data corresponds to the fourth time marker;
        based on each biomarker of a plurality of biomarkers, obtaining a plurality of first corresponding data corresponding to the third time marker from the third brain MRI data in the plurality of historical data, and obtaining a plurality of second corresponding data corresponding to the fourth time marker from the fourth brain MRI data;
        selecting a plurality of training biomarkers from the biomarkers according to a selection algorithm;
        obtaining a plurality of biomarker change data based on the plurality of first corresponding data and the plurality of second corresponding data of each training biomarker;
        obtaining a plurality of historical neuropsychological change data based on the third neuropsychological assessment score and the fourth neuropsychological assessment score in each group of historical data; and
        training the neural network module by using the plurality of biomarker change data, the plurality of historical neuropsychological change data, and the Alzheimer's marker of each group of historical data.

2. The system for Alzheimer's disease prediction using the neural network according to claim 1, wherein the processor obtains the plurality of hippocampal subfield curvature change data of the plurality of hippocampal subfields according to a change data computing procedure, the first brain MRI data, and the second brain MRI data, the change data computing procedure comprising:
    for each of the hippocampal subfields, obtaining a plurality of first curvature data from the first brain MRI data, and obtaining a plurality of second curvature data from the second brain MRI data; and
    for each of the hippocampal subfields, deducting each of the plurality of second curvature data by a first corresponding data in the plurality of first curvature data, and dividing the result by the first corresponding data, to obtain the plurality of hippocampal subfield curvature change data of the plurality of hippocampal subfields.

3. The system for Alzheimer's disease prediction using the neural network according to claim 2, wherein each of the plurality of first curvature data is selected from a group consisting of a maximum principal curvature, a minimum principal curvature, and a ratio of principal curvatures; and each of the plurality of second curvature data is selected from a group consisting of a maximum principal curvature, a minimum principal curvature, and a ratio of principal curvatures.

4. The system for Alzheimer's disease prediction using the neural network according to claim 1, wherein the processor obtains the plurality of hippocampal subfield volume change data according to a change data computing procedure, the first brain MRI data, and the second brain MRI data, the change data computing procedure comprising:
for each of the hippocampal subfields, obtaining a first volume data from the first brain MRI data, and obtaining a second volume data from the second brain MRI data; and
for each of the hippocampal subfields, deducting the second volume data by the first volume data, and then dividing the result by the first volume data, to obtain the plurality of hippocampal subfield volume change data.

5. The system for Alzheimer's disease prediction using the neural network according to claim 1, wherein the processor obtains the plurality of hippocampal subfield surface area change data according to a change data computing procedure, the first brain MRI data, and the second brain MRI data, the change data computing procedure comprising:
for each of the hippocampal subfields, obtaining a first surface area data from the first brain MRI data, and obtaining a second surface area data from the second brain MRI data; and
for each of the hippocampal subfields, deducting the second surface area data by the first surface area data, and then dividing the result by the first surface area data, to obtain the plurality of hippocampal subfield surface area change data.

6. The system for Alzheimer's disease prediction using the neural network according to claim 1, wherein the processor obtains the neuropsychological change data according to a neuropsychological change data computing procedure, the first neuropsychological assessment score, and the second neuropsychological assessment score, the neuropsychological change data computing procedure comprising:
deducting the second neuropsychological assessment score by the first neuropsychological assessment score, and then dividing the result by the first neuropsychological assessment score, to obtain the neuropsychological change data.

7. The system for Alzheimer's disease prediction using the neural network according to claim 1, wherein each of the hippocampal subfields is selected from a group consisting of Parasubiculum, Presubiculum, Subiculum, CA1, CA3, CA4, GC-ML-DG, HATA, Fimbria, Molecular layer, Hippocampal fissure, and Hippocampal tail.

8. The system for Alzheimer's disease prediction using the neural network according to claim 1, wherein the first neuropsychological assessment score and the second neuropsychological assessment score are selected from a group consisting of scores of Mini-Mental State Examination (MMSE) and Clinical Dementia Rating (CDR).

9. The system for Alzheimer's disease prediction using the neural network according to claim 1, wherein the neural network module comprises a fully connected sublayer with a plurality of hidden layers or a convolutional neural network layer.

10. The system for Alzheimer's disease prediction using the neural network according to claim 1, wherein the processor obtains the plurality of historical neuropsychological change data according to a historical neuropsychological change data computing procedure, and the third neuropsychological assessment score and the fourth neuropsychological assessment score in each group of historical data, the historical neuropsychological change data computing procedure comprising:
deducting the fourth neuropsychological assessment score by the third neuropsychological assessment score in each group of historical data, and then dividing the result by the third neuropsychological assessment score, to obtain the plurality of biomarker change data.

11. The system for Alzheimer's disease prediction using the neural network according to claim 1, wherein the processor obtains the plurality of biomarker change data according to a biomarker change data computing procedure, and the plurality of first corresponding data and the plurality of second corresponding data of each training biomarker, the biomarker change data computing procedure comprising:
for each training biomarker, deducting each of the plurality of second corresponding data by a first corresponding data that is in the plurality of first corresponding data and corresponds to the second corresponding data, and then dividing the result by the first corresponding data, to obtain the plurality of biomarker change data.

12. The system for Alzheimer's disease prediction using the neural network according to claim 1, wherein the selection algorithm comprises the following steps:
calculating a p-value according to the plurality of first corresponding data and the plurality of second corresponding data for each biomarker, wherein the p-value is a value obtained by performing a t-test on the plurality of first corresponding data and the plurality of second corresponding data; and
selecting, according to a critical p-value, a biomarker with a p-value less than the critical p-value from the plurality of biomarkers to obtain the plurality of training biomarkers.

13. The system for Alzheimer's disease prediction using the neural network according to claim 1, wherein the selection algorithm comprises the following steps:
for each biomarker of the plurality of biomarkers, obtaining a plurality of first biomarker change data based on the plurality of first corresponding data and the plurality of second corresponding data;
creating a plurality of random forests for all biomarkers based on the plurality of first biomarker change data for each biomarker and the plurality of Alzheimer markers, wherein the number of the plurality of random forests is a first number and each of the plurality of random forests has a plurality of decision tree;
obtaining a ranking for the plurality of biomarkers based on a total Gini importance of the plurality of random forests; and
selecting, according to the ranking, a predetermined number of selected biomarkers from all the biomarkers to obtain the plurality of training biomarkers.

14. The system for Alzheimer's disease prediction using the neural network according to claim 1, wherein each biomarker is selected from a group consisting of volumes, surface areas, maximum principal curvatures, minimum principal curvatures, and ratios of principal curvatures of the plurality of hippocampal subfields, the plurality of hippocampal subfields being selected from a group consisting of Parasubiculum, Presubiculum, Subiculum, CA1, CA3, CA4, GC-ML-DG, HATA, Fimbria, Molecular layer, Hippocampal fissure, or Hippocampal tail.

15. A method for Alzheimer's disease prediction using a neural network performed by a processor, the method comprising:
   obtaining a first brain magnetic resonance imaging (MRI) data, a second brain MRI data, a first neuropsychological assessment score, and a second neuropsychological assessment score, wherein the first neuropsychological assessment score has a first time marker, the second neuropsychological assessment score has a second time marker, the first brain MRI data corresponds to the first time marker, and the second brain MRI data corresponds to the second time marker;
   obtaining a plurality of image feature data according to the first brain MRI data and the second brain MRI data, wherein each image feature data is selected from a group consisting of a plurality of hippocampal subfield curvature change data of a plurality of hippocampal subfields, a plurality of hippocampal subfield volume change data of the plurality of hippocampal subfields, and a plurality of hippocampal subfield surface area change data of the plurality of hippocampal subfields;
   obtaining a neuropsychological change data according to the first neuropsychological assessment score and the second neuropsychological assessment score; and
   obtaining an Alzheimer's disease prediction result according to a neural network module, the plurality of image feature data, and the neuropsychological change data, wherein the neural network module comprises a plurality of trained parameters;
   wherein the method further comprising executing a training procedure on the neural network module to obtain the plurality of trained parameters, the training procedure comprising:
   obtaining a plurality of groups of historical data, each group of historical data comprising a third brain MRI data, a fourth brain MRI data, a third neuropsychological assessment score, a fourth neuropsychological assessment score, and an Alzheimer's marker, wherein the third neuropsychological assessment score has a third time marker, the fourth neuropsychological assessment score has a fourth time marker, the third brain MRI data corresponds to the third time marker, and the fourth brain MRI data corresponds to the fourth time marker;
   based on each biomarker of a plurality of biomarkers, obtaining a plurality of first corresponding data corresponding to the third time marker from the third brain MRI data in the plurality of historical data, and obtaining a plurality of second corresponding data corresponding to the fourth time marker from the fourth brain MRI data;
   selecting a plurality of training biomarkers from the biomarkers according to a selection algorithm;
   obtaining a plurality of biomarker change data based on the plurality of first corresponding data and the plurality of second corresponding data of each training biomarker;
   obtaining a plurality of historical neuropsychological change data based on the third neuropsychological assessment score and the fourth neuropsychological assessment score in each group of historical data; and
   training the neural network module by using the plurality of biomarker change data, the plurality of historical neuropsychological change data, and the Alzheimer's marker of each group of historical data.

16. The method for Alzheimer's disease prediction using the neural network according to claim 15, further comprising:
   obtaining the plurality of historical neuropsychological change data according to a historical neuropsychological change data computing procedure, and the third neuropsychological assessment score and the fourth neuropsychological assessment score in each group of historical data, the historical neuropsychological change data computing procedure comprising:
   deducting the fourth neuropsychological assessment score by the third neuropsychological assessment score in each group of historical data, and then dividing the result by the third neuropsychological assessment score, to obtain the plurality of biomarker change data.

17. The method for Alzheimer's disease prediction using the neural network according to claim 15, further comprising:
   obtaining the plurality of biomarker change data according to a biomarker change data computing procedure, and the plurality of first corresponding data and the plurality of second corresponding data of each training biomarker, the biomarker change data computing procedure comprising:
   for each training biomarker, deducting each of the plurality of second corresponding data by a first corresponding data that is in the plurality of first corresponding data and corresponds to the second corresponding data, and then dividing the result by the first corresponding data, to obtain the plurality of biomarker change data.

18. The method for Alzheimer's disease prediction using the neural network according to claim 15, wherein the selection algorithm comprises the following steps:
   calculating a p-value according to the plurality of first corresponding data and the plurality of second corresponding data for each biomarker, wherein the p-value is a value obtained by performing a t-test on the plurality of first corresponding data and the plurality of second corresponding data; and
   selecting, according to a critical p-value, a biomarker with a p-value less than the critical p-value from the plurality of biomarkers to obtain the plurality of training biomarkers.

19. The method for Alzheimer's disease prediction using the neural network according to claim 15, wherein the selection algorithm comprises the following steps:
   for each biomarker of the plurality of biomarkers, obtaining a plurality of first biomarker change data based on the plurality of first corresponding data and the plurality of second corresponding data;
   creating a plurality of random forests for all biomarkers based on the plurality of first biomarker change data for each biomarker and the plurality of Alzheimer markers, wherein the number of the plurality of random forests is a first number and each of the plurality of random forests has a plurality of decision tree;
   obtaining a ranking for the plurality of biomarkers based on a total Gini importance of the plurality of random forests; and
   selecting, according to the ranking, a predetermined number of selected biomarkers from all the biomarkers to obtain the plurality of training biomarkers.

20. The method for Alzheime's disease prediction using the neural network according to claim 15, wherein each biomarker is selected from a group consisting of volumes, surface areas, maximum principal curvatures, minimum principal curvatures, and ratios of principal curvatures of the plurality of hippocampal subfields, the plurality of hippocampal subfields being selected from a group consisting of Parasubiculum, Presubiculum, Subiculum, CA1, CA3, CA4, GC-ML-DG, HATA, Fimbria, Molecular layer, Hippocampal fissure, or Hippocampal tail.

21. A computer-readable recording medium with a stored program, when a computer loads and executes the stored program, performing the method according to claim 15.

22. A computer program product comprising a non-transitory computer readable medium having stored therein computer executable instructions for enabling at least one processor in a computer system to perform the method according to claim 15.

* * * * *